United States Patent [19]

Bellinger

[11] Patent Number: 4,670,618

[45] Date of Patent: Jun. 2, 1987

[54] PROCESS FOR IMPROVED RECOVERY OF PARAXYLENE

[75] Inventor: Carnot E. Bellinger, Sweeny, Tex.

[73] Assignee: Phillips Petroleum Company, Bartlesville, Okla.

[21] Appl. No.: 827,547

[22] Filed: Feb. 10, 1986

[51] Int. Cl.⁴ .......................... C07C 7/12; C07C 15/08
[52] U.S. Cl. .................................... 585/478; 585/805; 585/828
[58] Field of Search ............... 585/820, 828, 833, 835, 585/805, 802, 478; 208/310 Z, 321, 311

[56] References Cited

U.S. PATENT DOCUMENTS

| | | | |
|---|---|---|---|
| 2,632,779 | 3/1953 | Pfennig | 585/478 |
| 2,890,252 | 6/1959 | Cottle | 585/478 |
| 2,988,575 | 6/1961 | Hays et al. | |
| 3,636,121 | 11/1969 | Stine et al. | 585/828 X |
| 3,636,180 | 1/1972 | Broughton | |
| 3,813,452 | 5/1974 | Bleser | |
| 4,039,599 | 8/1977 | Gewartowski | 585/478 |
| 4,101,594 | 7/1978 | Howard, Jr. | |
| 4,139,571 | 2/1979 | Riemh | 585/478 |

FOREIGN PATENT DOCUMENTS 1354716 5/1974 United Kingdom ................ 585/805

Primary Examiner—Glenn Caldarola
Attorney, Agent, or Firm—Laney, Dougherty, Hessin & Beavers

[57] ABSTRACT

An improved process for concentration, separation and formation of paraxylene of the type wherein a hydrocarbon feed such as reformate is subjected to solvent extraction, fractionation and then Parex adsorption to remove paraxylene. The adsorber raffinate is isomerized to produce more paraxylenes and then recycled to the adsorber to remove the newly formed paraxylenes from the isomerization. The improvement includes a step of removing a stream from the process, downstream of the isomerization and introducing this stream upstream of the solvent extraction so that the concentration of non-aromatic such as naphthenes and paraffins produced in the isomerization will be reduced.

11 Claims, 1 Drawing Figure

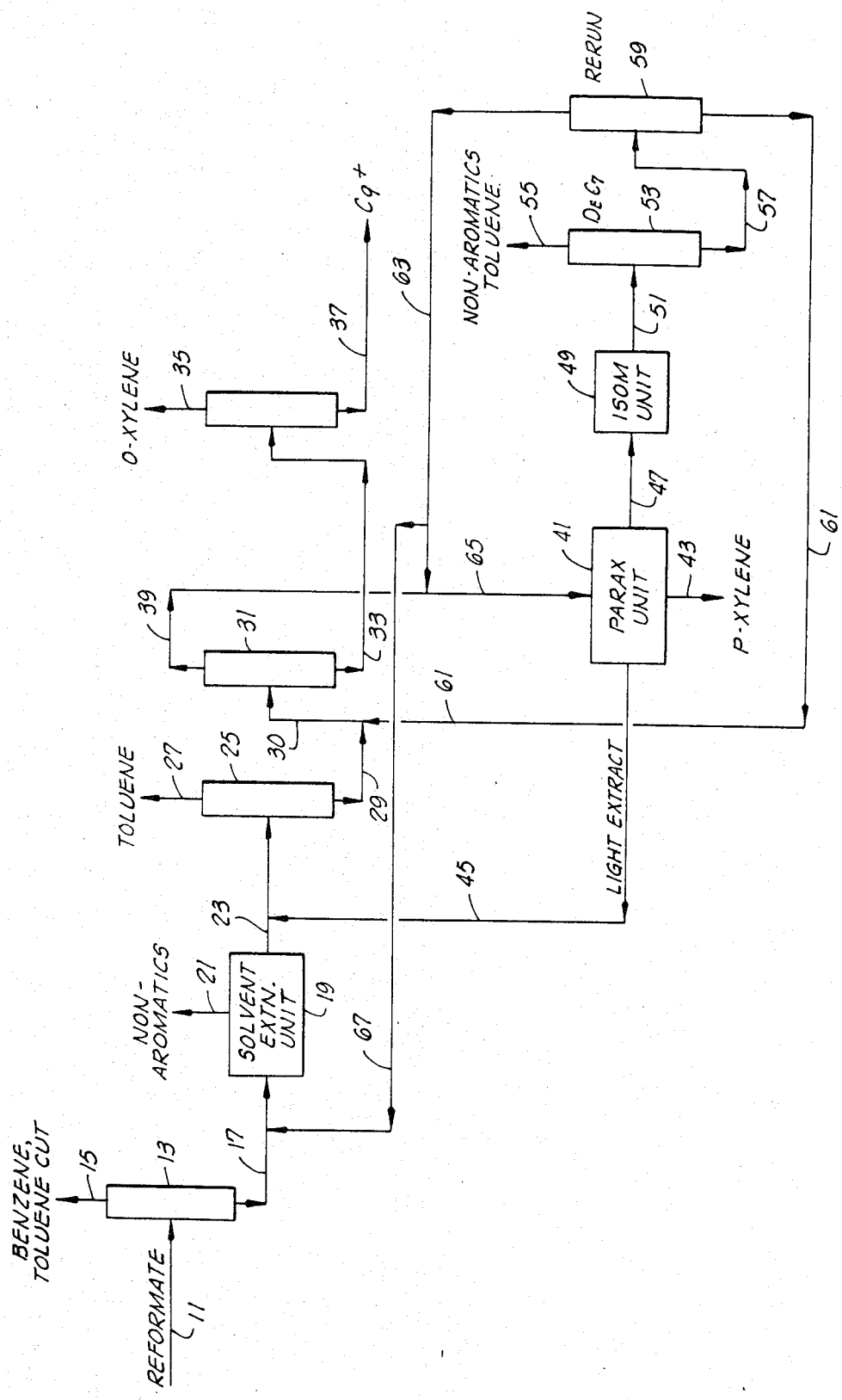

PROCESS FOR IMPROVED RECOVERY OF PARAXYLENE

BACKGROUND OF THE INVENTION

1. Field of the Invention

The present invention relates to processes for recovering paraxylene from mixtures of aromatic compounds and more particularly to such processes which isomerize and recycle the raffinate from an adsorption process for recovering paraxylene.

2. Description of the Prior Art

In the processing of hydrocarbons, such as oil, it is desirable to form, concentrate and remove paraxylene since paraxylene is a relatively more valuable hydrocarbon. A typical hydrocarbon mixture containing paraxylene and which is usually processed to obtain concentrated paraxylene is reformate from thermal or catalytic reforming processes. These reforming processes are used to form aromatic hydrocarbons from non-aromatic hydrocarbons.

In processing reformate to concentrate and separate paraxylene it is first subjected to solvent extraction to remove non-aromatics and then fractionated to form a $C_8$ aromatic concentrated material. This material is then subjected to an adsorption process to remove an essentially pure paraxylene product from the $C_8$ aromatic concentrated material. An adsorption process for paraxylene now used in the art is known as the Parex process. The raffinate from this adsorption process is isomerized to produce paraxylene from the $C_8$ isomers in the raffinate and the product of isomerization is recycled to the adsorption process for removing the newly formed paraxylene. Usually the isomerized raffinate is fractionated to concentrate the $C_8$ aromatics and then recycled to the Parex unit.

A problem with the paraxylene formation, concentration and removal processes of the prior art has been that isomerization converts some of the aromatic compounds to non-aromatics such as naphthenes and paraffins. These materials are difficult to fractionate from the recycle to the adsorption process and so build up in the recycle stream. This build up of non-aromatics increases until the fractionization can prevent any further build up. This increased concentration reduces the efficiency of the adsorption and isomerization and reduces the yield of paraxylene from the process as a whole.

It is accordingly an object of the present invention to provide a process which improves the recovery of paraxylene from hydrocarbon mixtures such as reformate. It is also an object of the present invention to provide such an improved process which does not require significant new equipment or expensive steps.

SUMMARY OF THE INVENTION

In accordance with the objects of the present invention, an improved process for separation of aromatic materials from reformate or the like is provided. The present invention improves upon processes of the type wherein non-aromatic materials are removed from reformate or the like in a solvent extraction step to form an aromatic concentrated reformate, the aromatic concentrated reformate is fractionated to $C_8$ concentrated reformate, and an adsorption and isomerization process removes paraxylene from the $C_8$ concentrated aromatic reformate and isomerizes the raffinate. The isomerization of the raffinate forms a recycle containing the non-isomerized raffinate and isomerized materials including paraxylene, naphthenes and paraffins. The recycle is returned to the adsorption and isomerization steps. The improvement comprises removing a portion of the recycle material containing naphthenes and paraffins from the isomerization and combining this portion with the feed to the solvent extraction. This step reduces the naphthenes and paraffins in the recycle to the adsorber below the reduction possible by fractionation and so improves the efficiency of the process and the yield of the paraxylene recovery. Preferably, the amount of the recycle conveyed to solvent extraction is in the range of from about one to about fifteen volume percent of the amount isomerized.

For a further understanding of the invention and further objects, features and advantages thereof, reference may be had to the following description taken in conjunction with the accompanying drawings.

BRIEF DESCRIPTION OF THE DRAWING

The FIGURE schematically shows a process performed in accordance with the present invention.

DESCRIPTION OF THE PREFERRED EMBODIMENTS

Referring now to the FIGURE, a paraxylene formation concentration and removal process is shown schematically. A mixture of hydrocarbons such as reformate from thermal reforming or catalytic reforming processes is introduced to the process in a stream 11. This stream contains aromatics including paraxylene and non-aromatics.

The stream 11 first enters a fractionator 13. Fractionator 13 separates toluene and lighter materials from the heavier, higher boiling point materials. The toluene and lighter materials form an overhead stream 15 and the heavier materials form a bottoms stream 17. The bottoms stream from the fractionator 17 is conveyed to a solvent extraction unit such as a sulfolane aromatic extractor. Most of the non-aromatic hydrocarbons leave the solvent extraction unit in a non-aromatics concentrated stream 21 and most of the aromatics leave the solvent extraction unit in an aromatics concentrated stream 23.

The aromatics stream 23 is conveyed to a fractionator 25 where toluene is removed. A toluene stream 27 exits overhead and a heavy aromatics stream 29 exits the bottom of the fractionator 25. The heavy aromatics stream 29 is further fractionated in a fractionator 31. The fractionator 31 removes orthoxylenes and heavier aromatics in a bottoms stream 33 which is still further fractionated to form an orthoxylene products stream 35 and a $C_9$ and heavier products stream 37.

The overhead of the fractionator 31 is a $C_8$ aromatics concentrated stream 39 which is conveyed to a Parex unit 41. Parex units are well-known in the art and include an adsorption process for producing high recovery (90–95%) and high purity (99% and greater) paraxylene from $C_8$ aromatic concentrated hydrocarbons. Thus, a highly concentrated paraxylene stream 43 exits the Parex unit and is the main product stream of the process. The Parex unit 41 also separates the raffinate from the adsorption process into a light extract stream 45 of lighter aromatics and a heavy extract stream 47 of heavier aromatics. The light extract stream 45 is recycled to stream 23 for fractionation in fractionators 25 and 31 and recycled to the Parex unit 41.

The heavy extracts stream 47 is conveyed to an isomerization unit 49. Devices for isomerization of heavy $C_8$ aromatic compounds to produce paraxylene are well-known in the art. Generally, 18 to 19 volume percent of the $C_8$ aromatic isomers entering the isomerization unit 49 will be converted to paraxylene. An undesirable but unavoidable result of the isomerization is that approximately 1% of the aromatics in stream 47 are converted to non-aromatics such as naphthenes and paraffins by the isomerization. Thus, the stream 51 which leaves the isomerization unit 49 includes compounds which are not isomerized in the isomerization process from stream 47 and isomerized compounds which include paraxylene and non-aromatics such as naphthenes and paraffins.

To recover the paraxylenes which result from the isomerization or which were not separated in the Parex unit 41, stream 51 is fractionated and then recycled to the Parex unit 41. To optimize the fractionation, stream 51 is first conveyed to a deheptanizing fractionator 53 where non-aromatics and toluene are removed in an overhead stream 55. However, because of the difficulty of separating non-aromatics in the fractionator 53, some of the non-aromatics, including the naphthenes and paraffins resulting from the isomerization are not separated and are conveyed with the bottoms stream 57 of the deheptanizer fractionator 53. In fact, without the improvement of the present invention, the naphthenes and paraffins increase in concentration until the deheptanizer fractionator 53 is able to prevent any further increase in concentration.

The bottom stream 57 from the deheptanizer 53 is conveyed to a second recycle fractionator 59 which removes $C_9$ and heavier aromatics as a bottom stream 61 and a $C_8$ aromatics concentrated overhead stream 63. The $C_9$ and heavier aromatics stream containing some $C_8$ aromatics is recycled to stream 29 for refractionation in fractionator 31 and ultimately, therefore, the $C_8$ aromatics included in stream 61 are recycled to the Parex unit 41. The $C_8$ aromatics concentrated stream 63 is recycled to stream 39 for immediate recycle to the Parex unit 41.

To this point the process of separating paraxylene by solvent extraction, fractionation, adsorption, isomerization and recycle is known in the art. U.S. Pat. Nos. 4,101,594; 3,636,180; 2,988,575 and 3,813,452 show portions of this process and describe certain features of the process in more detail. As shown by the prior art and as is well-known in the art, this process results in a build up of non-aromatics such as naphthenes and paraffins resulting from the isomerization in the isomerization unit 49. This build up can be as much as 10 volume percent of the feed stream to the Parex unit downstream of the recycle stream 63 (stream 65).

The present invention improves the yield of paraxylene and reduces the concentration of non-aromatics such as naphthenes and paraffins in stream 65 by removing a portion of the recycle to the Parex unit and conveying it to the solvent extraction unit 19 where solvent extraction removes the non-aromatics more effectively than possible by fractionation. Any of the streams containing the naphthenes and paraffins formed from the isomerization 49 can be conveyed to the solvent extraction unit 19 to remove these non-aromatics. However, it is most desirable to recycle as small a volume as possible to the solvent extraction unit 19 to obtain a maximum removal of the naphthenes and paraffins. Accordingly, it is preferable to remove a portion of stream 63 as a slipstream 67 and introduce this to stream 17 which enters the solvent extraction unit 19.

The volume percent of stream 63 which is removed as a slipstream 67 and conveyed to stream 17 will vary according to the rate of nonaromatics production in the isomerization unit 49, the capacity of the various operating units and the economics of solvent extraction versus the yield of paraxylene. In order to have a significant effect in reducing the non-aromatics in stream 65, at least one volume percent of the hydrocarbons isomerized and recycled to the Parex unit 41 must be conveyed in stream 67. Based on present economics, a preferable range of recycle in stream 67 is from about one volume percent of the hydrocarbons recycled to the Parex unit to about fifteen volume percent of the hydrocarbons recycled to the Parex unit. Most preferably the range is from five volume percent to ten volume percent.

EXAMPLES

Table I shows an example of stream compositions in a process as described above but which does not include the recycle slipstream 67 of the present invention. The volumes in barrels per hour and compositions in volume percent for various pertinent streams are shown.

TABLE I

| | Without Extractor Recycle Liquid Volume % | | | | | | | | |
|---|---|---|---|---|---|---|---|---|---|
| Stream No. | 65 Adsorber Feed | 47 Adsorber Raffinate | 51 Isomate | 57 Aromatics Concentrate | 63 Xylene Recycle | 39 Mixed Xylenes | 61 Heavy Aromatics | 29 Ext. Fract. Bottoms | 30 Xylene Col. Feed |
| Non-aromatics | 8.3 | 10.0 | 11.0 | 9.5 | 10.0 | 2.1 | — | 1.7 | 1.9 |
| Toluene | 1.2 | 1.0 | 2.0 | 1.0 | 1.2 | 1.2 | — | 1.0 | 1.1 |
| Ethylbenzene | 12.4 | 15.0 | 10.9 | 11.1 | 11.7 | 15.1 | 3.3 | 12.8 | |
| P—xylene | 18.4 | 2.0 | 17.7 | 18.1 | 19.1 | 15.8 | 3.3 | 12.3 | 13.3 |
| M-xylene | 43.1 | 52.0 | 40.3 | 41.8 | 43.9 | 40.6 | 16.7 | 32.9 | 34.6 |
| O—xylene | 16.6 | 20.0 | 16.5 | 16.9 | 14.1 | 25.2 | 16.7 | 31.0 | 32.6 |
| $C_9$ + Aromatics | | | 1.5 | 1.6 | — | | 60.0 | 9.3 | 3.7 |
| Totals | 100.0 | 100.0 | 100.0 | 100.0 | 100.0 | 100.0 | 100.0 | 100.0 | 100.0 |
| BBL/HR | 26.6 | 21.1 | 23.2 | 22.6 | 22.0 | 4.6 | 0.6 | 6.0 | 5.4 |

Table II shows the stream conditions of the same process when approximately 10% of stream 63 is removed as a slipstream 67 to the solvent extraction unit 19. The only difference between the two processes is the recycle stream 67 to the solvent unit 19. The reformate compositions and feed rates are the same. Tables I and II both give conditions after the process has run continuously so that steady state conditions in the recycles are reached.

TABLE II

| | | | | | With Extractor Recycle Liquid Volume % | | | | | |
|---|---|---|---|---|---|---|---|---|---|---|
| Stream No | 65 Adsorber Feed | 47 Adsorber Raffinate | 51 Isomate | 57 Aromatics Concentrate | 63 Xylene Recycle | 39 Mixed Xylenes | 67 Recyc to Extraction | 61 Heavy Aromatics | 29 Ext. Fract. Bottoms | 30 Xylene Col. Feed |
| Non-aromatics | 3.1 | 1.7 | 4.2 | 3.8 | 3.9 | 0.3 | 3.9 | — | 0.3 | 0.3 |
| Toluene | 1.0 | 0.6 | 2.1 | 1.0 | 1.0 | 0.9 | 1.0 | — | 1.0 | 0.9 |
| Ethylbenzene | 12.7 | 15.9 | 11.7 | 11.9 | 12.2 | 14.5 | 12.2 | 2.9 | 12.0 | 11.2 |
| P—xylene | 19.3 | 1.7 | 19.1 | 19.4 | 19.8 | 17.6 | 19.8 | 2.9 | 12.5 | 11.7 |
| M-xylene | 44.5 | 55.8 | 43.4 | 44.2 | 44.0 | 43.3 | 45.0 | 14.7 | 33.3 | 31.7 |
| O—xylene | 19.4 | 24.3 | 17.8 | 18.0 | 18.1 | 23.4 | 18.1 | 14.7 | 31.4 | 30.1 |
| $C_9$ + Aromatics | | | 1.7 | 1.7 | — | | | | 9.5 | 14.1 |
| Totals | 100.0 | 100.0 | 100.0 | 100.0 | 100.0 | 100.0 | 100.0 | 100.0 | 100.0 | 100.0 |
| BBL/HR | 29.7 | 23.7 | 26.4 | 26.0 | 25.3 | 6.9 | 2.5 | 0.7 | 5.9 | 6.5 |

As can be seen by reviewing Tables I and II the present invention achieves a substantial reduction of the non-aromatics in the feed stream 65 to the Parex unit 41 (8.3 volume percent reduced to 3.1 volume percent). The paraxylene present in the stream increases from 18.4 volume percent to 19.3 volume percent so that the yield of paraxylene from the Parex unit increases accordingly. Thus, approximately a 4.5 percent increase in yield of paraxylene results from the use of the present invention in the examples.

The above description and examples show a continuous process and the present invention will be most advantageously used with continuous processes. However, it will also have an advantage in non-continuous processes to the extent such non-continuous processes allow a build up of non-aromatics in the recycle to the adsorber.

As can be seen by the above description and examples, the improved process of the present invention is well adapted to achieve the objects and advantages mentioned as well as those inherent therein. While presently preferred embodiments of the present invention have been described for the purpose of this disclosure, numerous changes in the steps of the invention can be made by those skilled in the art, which changes are encompassed within the spirit of this invention as defined by the appended claims.

The foregoing disclosure and the showings made in the drawings are merely illustrative of the principles of this invention and are not to be interpreted in a limiting sense.

What is claimed is:

1. An improved process for separation of aromatic compounds including paraxylene from reformate or the like, or the type wherein non-aromatic materials are removed from reformate in a solvent extraction step to form an aromatic concentrated reformate, the aromatic concentrated reformate is fractionated to form a $C_8$ concentrated reformate, an adsorption and isomerization process removes paraxylene from the $C_8$ aromatic concentrated reformate and isomerizes the raffinate of the adsorption to form an isomerization product containing remaining $C_8$ aromatic concentrated reformate and paraxylene, naphthenes and paraffins formed from isomerization, and the isomerization product is recycled to the adsorption and isomerization step; the improvement comprising:
   removing a portion of said isomerization product and combining said portion with said reformate in said solvent extraction step so as to reduce the concentration of naphthenes and paraffins in said isomerization product.

2. The process of claim 1 wherein said portion of said isomerization product combined with said reformate is in the range of from about one volume percent of said isomerization product to about fifteen volume percent of said isomerization product.

3. The process of claim 2 wherein said portion of said isomerization product combined with said reformate is in the range of from about five volume percent of said isomerization product to about 10 volume percent of said isomerization product.

4. The process of claim 1 wherein the process includes fractionating the isomerization product to form a $C_8$ concentrated isomerization product and wherein the step of removing a portion of the isomerization product comprises removing a portion of said $C_8$ concentrated isomerization product.

5. An improved continuous process for separation of aromatic compounds including paraxylene from a charge stream mixture of hydrocarbons including non-aromatics and aromatics of the type wherein non-aromatic materials are removed from the charge stream in a solvent extraction step to form an aromatic concentrated stream, the aromatic concentrated stream is fractionated to form a $C_8$ concentrated stream, adsorption and isomerization steps remove paraxylene from the $C_8$ concentrated stream and isomerize the raffinate from the adsorption to form an isomerization product stream containing non-isomerized raffinate and isomerized paraxylene, naphthenes and paraffins, and the isomerization product stream is recycled to the streams downstream of the solvent extraction step; the improvement comprising:
   removing a portion of said isomerization product stream and forming a solvent extraction recycle stream therefrom which is combined with said charge stream to said solvent extraction step so as to reduce the concentration of naphthenes and paraffins in said recycle stream.

6. The process of claim 5 wherein said portion of said isomerization product combined with said charge stream is in the range of from about one volume percent of said isomerization product to about 15 volume percent of said isomerization product.

7. The process of claim 5 wherein said portion of said isomerization product combined with said charge stream is in the range of from about five volume percent of said isomerization product to about 10 volume percent of said isomerization product.

8. A continuous process for concentration, separation and formation of paraxylene comprising the steps of:

introducing an adsorber feed stream containing a substantial portion of paraxylene and other aromatic materials to an paraxylene adsorber to form a stream of substantially pure paraxylene and a raffinate stream containing a substantial portion of $C_8$ aromatic concentrated compounds;

isomerizing to paraxylene and non-aromatic compounds said raffinate stream to form a recycle stream;

recycling a first portion of said recycle stream to said adsorber;

forming a solvent extraction stream from a second portion of said recycle stream and extracting, by solvent extraction, non-aromatic compounds from said solvent extraction stream, the remainder of said stream after solvent extraction forming a second recycle stream;

recycling said second recycle stream to said adsorber; and continuously repeating the above steps.

9. The process of claim 8 wherein said solvent extraction stream is in the range of from about one volume percent of said recycle stream to about fifteen volume percent of said recycle stream.

10. The process of claim 8 wherein said solvent extraction stream is in the range of from about five volume percent to about fifteen volume percent of said recycle.

11. The process of claim 5 wherein prior to recycling said isomerization product stream to said streams downstream of said solvent extraction step, said isomerization product stream is fractionated to form a $C_8$ concentrated isomerization product stream, and wherein said step of removing a portion of said isomerization product stream comprises removing a portion of said $C_8$ concentrated isomerization product stream.

* * * * *

UNITED STATES PATENT AND TRADEMARK OFFICE
CERTIFICATE OF CORRECTION

PATENT NO. : 4,670,618

DATED : June 2, 1987

INVENTOR(S) : Carnot E. Bellinger

It is certified that error appears in the above-identified patent and that said Letters Patent are hereby corrected as shown below:

Column 5, line 53, change "or" to --of--.

Signed and Sealed this

Seventeenth Day of May, 1988

*Attest:*

DONALD J. QUIGG

*Attesting Officer*  *Commissioner of Patents and Trademarks*